United States Patent [19]
Burgoyne

[11] Patent Number: 5,976,572
[45] Date of Patent: *Nov. 2, 1999

[54] DRY SOLID MEDIUM FOR STORAGE AND ANALYSIS OF GENETIC MATERIAL

[75] Inventor: Leigh Alexander Burgoyne, Mitcham, Australia

[73] Assignee: Flinders Technologies Pty. Ltd., Australia

[*] Notice: This patent is subject to a terminal disclaimer.

[21] Appl. No.: 08/979,833

[22] Filed: Nov. 26, 1997

Related U.S. Application Data

[63] Continuation of application No. 08/480,135, Jun. 7, 1995, Pat. No. 5,756,126, which is a continuation-in-part of application No. 08/159,104, Nov. 30, 1993, Pat. No. 5,496,562, which is a continuation of application No. 07/671,859, May 29, 1991, abandoned.

[51] Int. Cl.$^6$ .............................. A61K 9/14; A61K 9/16; C12Q 1/68; C12P 19/34
[52] U.S. Cl. ...................... 424/488; 424/486; 424/489; 424/490; 435/6; 435/91.2; 536/23.1; 536/24.3; 536/24.33
[58] Field of Search .................. 424/488, 489, 424/486, 490; 435/6, 91.2; 536/23.1, 24.3, 24.33

[56] References Cited

U.S. PATENT DOCUMENTS

| | | |
|---|---|---|
| Re. 35,716 | 1/1998 | Stapleton et al. ............ 435/6 |
| 3,418,079 | 12/1968 | Rey et al. . |
| 3,616,259 | 10/1971 | Beutler . |
| 4,277,249 | 7/1981 | Broughton . |
| 4,299,916 | 11/1981 | Litman et al. . |
| 4,455,370 | 6/1984 | Bartelsman et al. . |
| 4,667,054 | 5/1987 | White et al. . |
| 4,789,630 | 12/1988 | Bloch et al. . |
| 4,895,795 | 1/1990 | Frazier et al. . |
| 4,965,190 | 10/1990 | Woo et al. . |
| 5,057,410 | 10/1991 | Kawasaki et al. . |
| 5,089,387 | 2/1992 | Tsay et al. . |
| 5,092,466 | 3/1992 | Anderson . |
| 5,128,247 | 7/1992 | Koller ...................... 435/91.1 |
| 5,188,963 | 2/1993 | Stapleton ................... 435/6 |
| 5,281,516 | 1/1994 | Stapleton et al. ............ 435/6 |
| 5,346,672 | 9/1994 | Stapleton et al. ............ 435/6 |
| 5,382,511 | 1/1995 | Stapleton ................... 435/6 |
| 5,432,097 | 7/1995 | Yourno . |
| 5,436,129 | 7/1995 | Stapleton ................... 435/6 |
| 5,451,500 | 9/1995 | Stapleton ................... 435/6 |
| 5,496,562 | 3/1996 | Burgoyne . |

FOREIGN PATENT DOCUMENTS

| | | |
|---|---|---|
| B 30256/84 | 1/1985 | Australia . |
| 0 130 523 A2 | 1/1985 | European Pat. Off. . |
| 0 221 308 A1 | 5/1987 | European Pat. Off. . |
| 0 261 955 A2 | 3/1988 | European Pat. Off. . |
| WO/90/03959 | 4/1990 | WIPO . |
| WO 91/07486 | 5/1991 | WIPO . |
| WO 93/07292 | 4/1993 | WIPO . |
| WO 93/19207 | 9/1993 | WIPO . |
| WO 94/26935 | 11/1994 | WIPO . |
| WO 96/11406 | 4/1996 | WIPO . |

OTHER PUBLICATIONS

Bruce E. Ames, et al. "Uric Acid Provides an Antioxidant Defense in Humans Against Oxidant–and Radical–Caused Aging and Cancer: A Hypothesis," *Proc. Nat'l. Acad. Sci. USA* 79(11):6858–6862 (Nov. 1981).

Leigh Burgoyne Ph.D., et al., Safe Collection, Storage and Anaylsis of DNA From Blood, *Abstract for Conference: 5th International Symposium on Human Identification*, Oct. 8–11, 1994.

Declan Butler, UK to set up DNA database of criminals . . . , *Nature* 370(6491):588–589 (Aug. 1994).

P. T. Gilham, "The Synthesis of Polynucleotide–Celluloses and Their Use in the Fractionation of Polynucleotide,:" *J. American Chem. Soc.* 86:4982–55 (Oct.–Dec. 1964).

Peter Gill, et al., "Forensic Application of DNA 'Fingerprints'", *Nature* 318:577–79 (1985).

M. Gross–Bellard, et al., "Isolation of High–Molecular–Weight DNA from Mammalian Cells," *Eur. J. Biochem.* 36:32–38 (Jul. 2, 1973).

Michael A. Harvey, et al., "Impregnated 903 Blood Collection Paper: A Tool for DNA Preparation from Dried Blood Spots for PCR Application".

Innis et al., "RNA Processing: APO–B," by Lyn M. Powell, *PCR Protocols* Chapter 29, pp. 237–244 (1990).

L. Jervis, et al., "Purification of Ribonuclease $T_1$ on Porous Glass Affinity Adsorbents", *J. of Chromatography* 97(1):33–38 (Oct. 1974).

Kwok–Wai Lam, et al., "Inhibition of Ascorbate Oxidation by Urate", *J. Inorganic Biochemistry*, 22(4):241–248 (1984).

Linda Madisen, et al., "DNA Banking: The Effects of Storage of Blood Isolated DNA on the Integrity of DNA", *American J. of Med. Gen.* 27(2):379–390 (1987).

T. Maniatis, et al., "Molecular Cloning—A Laboratory Manual" *Cold Spring Harbor Laboratory* Southern Transfer pp. 382–289, Preparations of Buffers and Solutions p. 447 (1982).

(List continued on next page.)

*Primary Examiner*—Stephanie W. Zitomer
*Attorney, Agent, or Firm*—Merchant, Gould, Smith, Edell, Welter & Schmidt, P.A.

[57] ABSTRACT

The present invention provides a dry solid medium for storage of genetic material, including RNA and DNA, in a form suitable for subsequent analysis. The invention also provides a dry solid medium including components which function in subsequent analysis of the genetic material using, for example, PCR, reverse transcriptase initiated PCR, LCR, RFLP, or genetic hybridization. The components for subsequent analysis include, for example, nucleotide sequences such as a primer and a target sequence stabilizer.

The invention further provides methods for using the dry solid medium of the invention. The invention and methods thereof are particularly suited for analysis in automated systems.

20 Claims, 3 Drawing Sheets

OTHER PUBLICATIONS

Stuart L. Marcus, "Purification of Avian Myeloblastosis Virus DNA Polymerase by Affinity Chromatography on Polycytidylate–Agarose", *J. of Virology* 14(4):853–859 (Oct. 1974).

Edward R.B. McCabe, et al., "DNA Microextraction from Dried Blood Spots on Filter Paper Blotters: Potential Applications to Newborn Screening", *Hum. Gent.* 75(3):213–216 (Mar. 1987).

Mohindar S. Poonian, "Covalent Attachment of Nucleic Acids to Agarose for Affinity Chromatography", *Biochemistry* 10(3):424–427 (1971).

B. Singer, et al., "Effects of Light in the Presence of Iron Salts on Ribonucleic Acid and Model Compounds" *Biochemistry* 4(2):226–233 (Feb. 1965).

Patrick E. Williams, et al., "Evaluation of a Novel Matrix for the Analysis of DNA and its Application to Automated DNA Sample Processing", *Abstract for Conference: 5th International Symposium on Human Identification*, (Oct. 8–11, 1994).

Declaration of Michael J. Kvasnik (w/Exhibits A–F).

Nancy R. Webb, et al., "Purification of the Messenger RNA Cap–Binding Protein Using New Affinity Medium", *Biochemisty* 23(2):177–181 (Jan. 1984).

International Search Report and Annex to International Search Report for International Application No. PCT/AU 89/00430.

Promotional Letter from Schleicher & Schuell, dated Jul. 31, 1995.

"UltraPAK™ Customized DNA Collection Systems" brochure.

"UlstraSTAIN™ Blood Storage System" brochure.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

TGACTGAGTA CAAACTGGTG GTG                                               23

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:2:

CTCTATGGTG GGATCATATT CA                                                22

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TGGGCTGGAA TGGAAAGGAA TGCAAAC                                           27

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TCCATTCGAT TCCATTTTTT TCGAGAA                                           27

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GAATGTATTA GAATGTAATG AACTTTA                                           27

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TTCCATTCCA TTCCATTCCT TTCCTTT                                           27

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GTGCTGCAGG TGTAAACTTG TACCAG                                              26

(2) INFORMATION FOR SEQ ID NO:8:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:8:

CACGGATCCC GGTAGCAGCG GTAGAGTTC                                           29
```

DRY SOLID MEDIUM FOR STORAGE AND ANALYSIS OF GENETIC MATERIAL

CROSS-REFERENCE TO RELATED APPLICATIONS

The present application is a continuation application of U.S. Ser. No. 08/480,135, filed Jun. 7, 1995, now U.S. Pat. No. 5,756,126, which is a continuation-in-part of U.S. Ser. No. 08/159,104, filed Nov. 30, 1993, now U.S. Pat. No. 5,496,562, which is a continuation of U.S. Ser. No. 07/671,859, filed May 29, 1991, now abandoned, which applications are incorporated herein by reference.

FIELD OF THE INVENTION

The field of the present invention pertains to a dry solid medium and method for collection of genetic material in a form suitable for storage and/or subsequent analysis. The invention further provides for analysis of stored genetic material using methods which are suited for automated analyzing systems.

BACKGROUND

While blood containing genetic material to be anlayzed has typically been transported from the place of removal from a human or animal, to the place of analysis as purified genetic material, liquid whole blood, frozen whole blood or whole blood dried onto paper. All of these methods have disadvantages. Transport of genetic material in blood as dried, purified genetic material is most desirable, but it requires a high standard of technical assistance to be available at the place of removal from the human or animal. When technical assistance is not available at the place of removal, whole blood or other unpurified samples are usually sent to a central facility where the genetic material is purified.

Transport of liquid whole blood often involves the need for sterility of collection. Under some circumstances, this is extremely inconvenient, for example, where the sample is a heel-prick taken from an infant. The transport of liquid whole blood or frozen blood also demands temperature control and an appropriate transport system other than the regular postal system. This is true even before considering concerns about hygiene. In addition, problems with pathogens associated with whole blood, such as the HIV virus, generally rule out the transport of any potentially infectious liquid or frozen sample except under proper and expensive supervision.

Blood dried on filter paper is a proven alternative to the above procedures and it has been shown that genetic material can be extracted and isolated from dried whole blood spots in a form and in sufficient quantities for use in DNA analysis. McCabe, E. R. B., et al., "DNA Microextraction From Blood Spots on Filter Paper Blotters: Potential Screening Applications to Newborn Screening," *Hum. Genet.* 75:213–216 (1987). But, this procedure still suffers from a number of disadvantages. For example, typically, there has been no deliberate and rapid destruction of blood associated pathogens. This creates a potential hazard for blood handling personnel. In addition, usually, there has not been deliberate inhibition of the processes which degrade the genetic material other than that which may occur by desiccation. However, slow desiccation, or even a small degree of rehydration under conditions of high relative humidity, will allow the growth of DNA or RNA destroying microflora. Moreover, even in the presence of a bacteriostatic agent of the type that does not denature proteins, there are conditions that permit enzymatic-autolytic breakdown of the genetic material and some nonenzymatic breakdown of the genetic material. (Enzymatic-autolytic breakdown refers to the process whereby dying or damaged tissues, of either human, animal or parasite cells, activate enzymes that degrade their own components). Furthermore, there is typically considerable difficulty desorbing very high molecular weight DNA or RNA from paper, if this is required. Surface adsorption effects can cause losses of genetic material which may cause the preferential loss of the least degraded, i.e. the most desired class of DNA or RNA molecules.

Thus, there is a need for a safe, convenient and minimally labor intensive means for storage of a genetic material to be analyzed which is contained in a liquid sample.

However, even if a sample of genetic material is collected in a safe, convenient and reliable form for storage and subsequent analysis, there are also logistic problems which arise when there are many different types of analysis to be performed on a collected sample. For example, polymerase chain reaction (PCR) analysis requires a different primer-pair for each specific analysis to be performed. Obviously, the problems tend to further increase when multiple samples are submitted for analysis.

Present methods for in-situ-processing based on the use of oligonucleotide primers, for example, PCR, rely on the stored genetic material being heated and cooled in reaction mixtures that have primers added to them at the time of beginning temperature cycling. In many types of analysis of genetic material, it is the primers that determine the particular specificity of a reaction. Because there is usually a primer pair for each conceivable type of analysis, there are an extremely large number of possible primers (for example, all the sequences within the genes of humans, animals and all other living organisms including the pathogens of humans and animals). Thus, in any centralized facility which receives multiple samples for analysis of genetic material using, for example, oligonucleotide primers, the logistic problems can be immense.

Automation of analysis of genetic material allows for increased numbers of samples to be processed more efficiently. However, automation of the analysis of genetic material still requires the automated system to have completely separate delivery devices for each different set of primers. Otherwise, the cross-contamination which may occur will be impossible to control.

Thus, in general, if reactions like PCR are to be carried out at a centralized location using automated systems and using presently known methods, the range of different sequences which can be analyzed at one time will be restricted by the physical problems of keeping a clean delivery system of pipettes, etc., or by the molecular problems inherent in using mixtures of diverse primers. Clearly, circumvention of this restriction would be advantageous for analyzing multiple samples of genetic material for different genetic sequences.

SUMMARY OF THE INVENTION

The present invention provides a safe, convenient and minimally labor intensive apparatus and method for storage of a genetic material which is contained in a liquid medium. The invention further provides for storage of genetic material in such a way as to allow for simplified analysis of one or more samples of genetic material using automated systems.

The invention provides a dry solid medium for storage of a sample of genetic material. The dry solid medium of the invention is composed of a solid matrix and a composition which when applied to the dry solid medium protects against degradation of genetic material stored on the dry solid medium. The dry solid medium further provides for inactivation of microorganisms, including those which may be pathogenic to humans.

The composition of the dry solid medium includes a weak base, a chelating agent, an anionic detergent and optionally, uric acid or a urate salt.

According to the invention, genetic material stored on the dry solid medium may be analyzed using methods known in the art, for example, polymerized chain reaction (PCR), ligase chain reaction (LCR), reverse transcriptase initiated PCR, DNA or RNA hybridization techniques including restriction fragment length polymorphism (RFLP) and other techniques using genetic or DNA or RNA probes, genomic sequencing, enzymic assays, affinity labeling, methods of detection using labels or antibodies and other similar methods.

Genetic material stored on the dry solid medium of the invention may be analyzed in situ or after removal from the dry solid medium.

Another embodiment of the invention provides a dry solid medium for storage of a sample of genetic material and includes a component which is functional in the subsequent analysis to be performed on the stored sample of genetic material. According to the invention, components for subsequent analysis which may be included with a sample of genetic material include, for example, nucleotide sequences such as PCR primers, target sequence stabilizers, genetic probes, primers for genetic sequencing or sets of oligonucleotide substrates for LCR analysis.

The invention also provides methods for using the dry solid media of the invention. In one embodiment, the invention provides a method for storing a sample of genetic material on the dry solid medium in a substantially nondegraded form.

The invention further provides a method for storing a sample of genetic material and subsequently analyzing the stored sample of genetic material. According to this embodiment of the invention, the stored genetic material is preferably washed to remove any proteins or hemoglobin associated with a sample of genetic material or to remove any component of the composition of the dry solid medium which may inhibit subsequent analysis of the genetic material. The invention provides for the stored genetic material to be washed using either an aqueous or a nonaqueous washing system.

The aqueous and nonaqueous washing systems used to wash a sample of genetic material prior to analyzing the genetic material provide for removing protein, hemoglobin or components of the composition of the dry solid medium without substantially effecting the stored genetic material or any component included on the dry solid medium for subsequent analysis of the genetic material. In addition, the aqueous and nonaqueous wash systems of the invention may be used to wash genetic material which is stored, for example, on a solid matrix which does not have sorbed to it the DNA protecting composition of the invention.

The nonaqueous wash system of the invention includes contacting a sample of genetic material stored on the dry solid medium of the invention with a herein described single phase phenol solution. The single phase phenol solution is then removed from the dry solid medium containing a sample of genetic material and the dry solid medium containing a sample of genetic material is then contacted with an aqueous alcohol wash solution. The aqueous alcohol wash solution is removed and the dry solid medium containing the sample of genetic material may further be washed with an aqueous ionic solution. The washed sample of genetic material may then be analyzed by methods recited above.

A sample of genetic material stored on a dry solid media of the invention may also be analyzed using standard enzymic tests used, for example, to detect phenylketonuria (PKU) or galactosemia after neutralizing the effects of protein denaturing components of the dry solid medium using, for example, a converter solution.

The dry solid medium and the dry solid medium including components for subsequent analysis is particularly useful for analysis of a genetic sample using automated systems.

DETAILED DESCRIPTION OF THE INVENTION

The present invention provides a dry solid medium for collection of genetic material in a form suitable for storage and subsequent analysis. The invention further provides methods for subsequently analyzing the collected genetic material. The dry solid medium and methods of use, disclosed herein, provide a safe, convenient and reliable means for storing samples of genetic material in a manner which provides reliable accuracy of analytical results. Moreover, the invention provides for enhanced convenience and efficiency when multiple samples are analyzed using automated systems, for example, at a centralized analyzing facility.

In several places throughout the present specification guidance is provided through lists of examples. The inventors wish to make clear that in each instance, the recited lists serve only as representative groups. It is not meant, however, that the lists are exclusive.

As used herein, the phrase "genetic material" (GM) means either or both deoxyribonucleic acid (DNA) or ribonucleic acid (RNA). According to the invention, a sample of GM is collected on the dry solid medium by removing the sample from a source and applying the sample to the herein described dry solid medium. Methods for removing a sample of genetic material from a source are known in the art. For example, a sample of genetic material in blood may be removed from a human or animal source by venipuncture and the sample then applied to the dry solid medium of the invention.

As used herein a "sample of genetic material" or "sample of GM" includes a liquid having dissolved, suspended, mixed or otherwise contained therein, either or both DNA or RNA, cells which contain either or both DNA or RNA or cell components which contain either or both DNA or RNA. Once the sample of GM is applied to the dry solid medium, the liquid tends to evaporate (evaporation may be enhanced by a warm air dryer) leaving the DNA and/or RNA entrained to the dry solid medium in a dry form. The GM entrained to the dry solid medium in "dry form" may be purified DNA and/or RNA, semipurified DNA and/or RNA or DNA and/or RNA remaining in cells.

The sample of GM which is applied to the dry solid medium may be derived from any source. This includes, for example, physiological/pathological body liquids (e.g., secretions, excretions, exudates and transudates) or cell suspensions (e.g., blood, lymph, synovial fluid, semen, saliva containing buccal cells, skin scrapings, hair root cells, etc.) of humans and animals; physiological/pathological liquids or cell suspensions of plants; liquid products, extracts or suspensions of bacteria, fungi, plasmids, viruses etc.; liquid products, extracts or suspensions of parasites including helminths, protozoas, spirochetes, etc.; liquid extracts or homogenates of human or animal body tissues (e.g., bone, liver, kidney, etc.); media from DNA or RNA synthesis; mixtures of chemically or biochemically synthesized DNA or RNA; and any other source in which DNA and/or RNA is or can be in a liquid medium. Preferably, the liquid containing the GM evaporates after applying the sample to the dry solid medium leaving GM in dry form prior to subsequent analysis.

The dry solid medium of the invention provides for storage and/or subsequent analysis of the stored sample of GM. The dry solid medium is composed of a solid matrix having sorbed thereto a composition which can protect against degradation of the GM stored on the solid medium. The composition can also cause inactivation of microorganisms which may be associated with a sample of GM and which may be potentially pathogenic to human handlers of the stored sample of GM.

A solid medium and a composition sorbed to a solid matrix is disclosed in U.S. patent application Ser. No. 08/159,104 which has been incorporated herein by reference.

As used herein, the term "storing", "storage", "stored" and other derivatives of "store", when referring to GM in dry form entrained to the dry solid medium, means the preservation of GM in a form suitable for subsequent analysis and which has not undergone substantial degradation. The time period for which GM may be stored according to the invention may be as short as the time necessary to transport a sample of GM from the place of collection of the sample to the place where subsequent analysis is to be performed. The conditions under which the sample of GM may be stored on the dry solid medium of the invention varies. Typically, samples are stored at temperatures from −200° C. to 40° C. In addition, stored samples may optionally be stored in dry or dessicated conditions or under an inert atmosphere. Storage may be for a few minutes up to many years, preferably, about 10 minutes up to 100 years.

In another embodiment of the invention, the dry solid medium may further include a component which is functional in the subsequent analysis to be performed on the stored GM. Subseqent analysis which may be performed on a sample of GM stored on the dry solid medium includes analysis methods known in the art, for example, polymerase chain reaction (PCR), ligase chain reaction (LCR), reverse transcriptase initiated PCR, DNA or RNA hybridization techniques including restriction fragment length polymorphism (RFLP) and other techniques using genetic or DNA or RNA probes, genomic sequencing, enzymatic assays, affinity labeling, methods of detection using labels or antibodies and other similar methods. In a preferred embodiment, the dry solid medium of the invention is a suitable medium for storage of components for subsequent analysis which are included on the dry solid medium. In addition, the inventors recognize that many new analytical and diagnostic methods may be developed in the future for which the dry solid medium and method of the invention may be equally useful and which would fall within the spirit and scope of the claims appended hereto.

In the case of stored RNA, particularly unstable RNA, components for subsequent analysis which may be included may also provide protection against RNA degradation. This includes RNase inhibitors and inactivators, proteins and organic moieties that stabilize RNA or prevent its degradation.

Once the GM has been collected on the dry solid medium, it may be encased in a protective material, for example, a plastic film, which may further protect against GM degradation during storage. Subsequent analysis of the GM stored on the solid medium of the invention may be performed in situ on the solid medium or, alternatively, the GM may first be removed from the solid medium prior to subsequent analysis.

I. THE DRY SOLID MEDIUM

The dry solid medium of the invention includes a composition sorbed to a solid matrix. As used herein, the term "sorb" means that the composition of the invention is absorbed, adsorbed or otherwise incorporated into or onto the solid matrix in such a way as not to be readily removed from the matrix unless subjected to conditions which are intentionally or inadvertently performed to remove the sorbed composition from the solid matrix.

A solid matrix suitable for the dry solid medium and method of the invention includes any material to which the composition will sorb and which does not inhibit storage or subsequent analysis of the GM applied to the dry solid medium. This includes flat dry matrices or a matrix combined with a binder to form a pellet or tablet to which the composition is sorbed. In one preferred embodiment, the solid matrix is of a porous nature to provide entrainment of the GM onto the dry solid medium. As used herein the term "entrain", means that during storage the GM is bound to the dry solid medium without substantial reliance on ionic, covalent or van der waals interactions. A solid matrix suitable for this purpose includes, but is not limited to, a matrix which is cellulose based (e.g., cellulose, nitrocellulose or carboxymethylcellulose papers), hydrophilic polymers including synthetic hydrophilic polymers (e.g., polyester, polyamide, carbohydrate polymers), polytetrafluroethylene (Empore™, 3M, St. Paul, Minn.), fiberglass and porous ceramics.

GM may also be collected on a solid matrix which lacks the below-described composition of the invention. In addition, a component for subsequent analysis of a sample of GM may also be included on a solid matrix which lacks the composition of the invention. Furthermore, hemoglobin or proteins associated with a sample of GM may be removed from a sample of GM stored on a solid matrix which does or does not include a component for subsequent analysis of the stored GM using an aqueous or nonaqueous (e.g., below-described single phase phenol wash) extraction procedure. However, by using only a solid matrix for storage, the GM protecting and pathogen inactivation effects of the composition of the invention obviously will not be available to the GM or components for subsequent analysis.

To form the dry solid medium of the invention, a composition which protects against degradation of GM is sorbed to the solid matrix. As used herein, the phrase "protects against degradation of GM" means that the dry solid medium of the invention maintains the stored GM in a substantially nondegraded form. This provides a sample of GM suitable for many different types of subsequent analytical procedures. Protection against degradation of GM may include protection against substantial damaging of GM due to GM damaging events such as that caused by chemical or biological means including action of bacteria, viruses, free radicals, nucleases, ultraviolet radiation, oxidizing agents and acidic agents (e.g., pollutants in the atmosphere).

The composition sorbed to the solid matrix to form the dry solid medium of the invention may include one or more of a weak base, a chelating agent, or an anionic detergent or surfactant. In addition, the composition sorbed to the dry solid medium may also include uric acid or a urate salt.

As used herein, the "weak base" of the composition may be a Lewis base which has a pH of about 6 to 10, preferably about pH 8 to 9.5. One function of the weak base is to act as a buffer to maintain a composition pH of about 6 to 10, preferably about pH 8.0 to 9.5, for example, pH 8.6. Hence, a weak base suitable for the composition of the invention may, in conjunction with other components of the composition, provide a composition pH of 6 to 10, preferably, about pH 8.0 to 9.5. Suitable weak bases according to the invention include organic and inorganic bases. Suitable inorganic weak bases include, for example, an alkali metal carbonate, bicarbonate, phosphate or borate (e.g., sodium, lithium, or potassium carbonate). Suitable organic weak bases include, for example, tris-hydroxymethyl amino methane (Tris), ethanolamine, triethanolamine and glycine and alkaline salts of organic acids (e.g., trisodium citrate). A preferred organic weak base is a weak monovalent organic base, for example, Tris. The Tris may be either a free base or a salt, for example, a carbonate salt.

Although the inventors do not wish to be limited to a single theory, it is believed that the weak base may provide a variety of functions, including protecting the GM from degradation. In addition to providing a buffer system, it is also believed that the weak base can act to ensure proper action of the below described chelating agent in binding divalent metal ions. In addition, the weak base may also prevent the action of acid nucleases which may not be completely dependent on divalent metal ions for functioning.

The composition of the dry solid medium can also include a chelating agent. According to the invention, a preferred chelating agent is a strong chelating agent. By "strong" chelating agent it is meant that the agent binds multivalent metal ions with a comparable or better affinity than ethylene diamine tetraacetic acid (EDTA). A preferred chelating agent according to the invention is EDTA. Although the inventors do not wish to be limited to a particular theory, it is believed that one function of the chelating agent of the invention is to bind divalent ions which if present with the stored GM may partake in causing damage to the GM. Ions which may be chelated by the chelating agent include divalent active metal ions, for example, magnesium and calcium, and transition metal ions, for example, iron. Both calcium and magnesium are known to promote GM degradation by acting as co-factors for enzymes which may destroy GM (e.g., most known nucleases). In addition, transition metal ions, such as iron, may readily undergo oxidation and reduction and damage nucleic acids by the production of free radicals or by direct oxidation.

The composition of the dry solid medium can further include an anionic detergent or surfactant. As used herein, the terms "surfactant" and "detergent" are synonymous and may be used interchangeably. Although not wishing to be limited to a single theory, it is believed that the anionic surfactant of the invention functions to denature non-GM compounds, for example, proteins, which are associated with the stored GM. Accordingly, denaturation of protein is one function of the anionic surfactant. According to the invention, any anionic surfactant which binds to and denatures proteins may be suitable for the invention. A preferred anionic detergent is a strong anionic detergent. As used herein, a "strong" anionic detergent includes a hydrocarbon moiety, aliphatic or aromatic, containing one or more anionic groups. Particularly preferred anionic detergents suitable for the invention include sodium dodecyl sulphate (SDS) and sodium lauryl sarcosinate (SLS). In a preferred embodiment, the anionic detergent of the invention causes inactivation of most microorganisms which have protein or lipids in their outer membranes or capsids, for example, fungi, bacteria or viruses. This includes microorganisms which may be pathogenic to humans and are present in a sample of GM.

Inactivation of a microorganism is believed to result from destruction of the secondary structure of its external proteins, internal proteins and any protein containing membranes necessary for viability. The inventors recognize that the anionic detergent may not inactivate some forms of organisms, for example, highly resistant bacterial spores and extremely stable enteric virions. Moreover, the inventors further recognize that while it may be desirable to inactivate pathogenic microorganisms, the GM of a microorganism associated with the stored sample of GM is also amenable for storage on dry solid medium of the invention. This allows for storage and/or subsequent analysis of the GM of a microorganism associated with a stored sample of GM.

The composition of the invention may optionally include a uric acid or a urate salt. According to the invention, the longer the period of time for which the GM is to be stored the more likely that uric acid or a urate salt may need to be included in the composition sorbed to the solid matrix. However, even if the GM is only to be stored for a matter of minutes, it may still be desirable to incorporate uric acid or urate salts into the composition.

While the inventors do not wish to be limited to any single theory, it is believed that the uric acid or urate salt may provide many functions. For example, the uric acid or urate salt may be converted to allantoin in acting as a free radical trap that preferentially accepts free radicals that would otherwise damage the nucleotide guanine. The free radicals are believed to be generated by spontaneous oxidation of thio groups which are present, for example, in denatured serum protein of blood. Free radicals may also be generated due to oxidation or reduction of iron in blood. Because uric acid is a weak acid, it may also function as a component of the buffering system provided by the weak base as discussed above. In addition, the uric acid and urate salt may act as an erodible surface in that it is sparingly soluble so that a DNA sample dried onto its crystals will be released as the urate beneath erodes. Hence, the uric acid or urate salts may also provide for easy removal of a stored sample of GM if in situ processing is not desired.

Furthermore, after the sample of GM is applied to the dry solid medium, the dry solid medium with the applied sample of GM may be encased in a protective material, for example, a plastic film, which may further protect against degradation of stored GM. Examples of plastic films which are suitable according to the invention include polystyrene, polyethylene, polypropylene and other suitable lamination plastics. Encasing the dry solid medium in a protective material may be accomplished by methods known in the art. One simple method for encasing the dry solid medium in a plastic film is to put the dry solid medium into a container, e.g., a polyethylene bag, which is of sufficient size to hold the dry solid medium such that when a plastic film in liquid form is added to the container all parts of the dry solid medium will be coated by the liquid. The plastic film, in liquid form, is added to container to coat the dry solid medium. The liquid plastic film is allowed to dry to provide a plastic film coating which encases the dry solid medium. Prior to analysis, the plastic film is removed from the dry solid medium using methods known in the art, for example, dissolving with organic solvents such as chloroform or mechanical stripping.

The inventors further note that a dry solid medium including components for subsequent analysis (discussed below), with an applied sample of GM, may also be encased in a protective material as described above.

II. SUBSEQUENT ANALYSIS OF GENETIC MATERIAL STORED ON THE DRY SOLID MEDIUM

As used herein, "subsequent analysis" includes any analysis which may be performed on a sample of GM stored on the dry solid medium. The GM stored on the dry solid medium may be analyzed in vitro. The GM may first be removed from the dry solid medium prior to analysis. The sample of GM may be subjected to chemical, biochemical or biological analysis. Examples of subsequent analysis which may be performed on samples of GM stored on the dry solid medium include polymerase chain reaction (PCR), ligase chain reaction (LCR), reverse transcriptase initiated PCR, DNA or RNA hybridization techniques including restriction fragment length polymorphism (RFLP) and other techniques using genetic or DNA or RNA probes, or genomic sequencing. In addition, diagnostic procedures presently performed on whole blood samples, for example, the Guthrie test for phenyl-ketonuria (PKU) or enzymatic tests, for example, galactosemia may be performed on blood samples stored on the dry solid medium of the invention after first neutralizing the effects of protein denaturing components of the dry solid medium, for example, using a "converter solution."

GM stored on the dry solid medium of the invention may also serve as a template for subsequent analysis of the GM using PCR methods. This includes PCR using DNA or RNA as a template. When RNA is the GM to be analyzed, the RNA may serve as a template using reverse transcriptase initiated PCR. The DNA sequence produced from the RNA template may then serve as a template for further PCR amplification.

If the sample of GM is in whole blood, prior to analysis by PCR, LCR, RFLP, reverse transcriptase initiated PCR, genetic probing or other technique, hemoglobin or proteins associated with the GM are preferably removed from the sample of GM stored on the dry solid medium. Hemoglobin and/or proteins associated with the GM may be removed using methods known in the art, for example, aqueous or nonaqueous extraction procedures. In addition, some components of the composition of the invention (e.g., anionic detergent) are preferably removed, using aqueous or non-aqueous extraction procedures, prior to subsequent analysis.

In one preferred embodiment, hemoglobin, blood proteins or other proteins associated with a sample of GM may be removed using nonaqueous extraction procedures, for example, the below-described single phase phenol wash method. In addition, the single phase phenol wash may be followed with the below-described ionic aqueous alcohol wash to provide ions necessary for subsequent PCR, LCR or similar analysis of GM stored on the dry solid medium.

Methods for PCR, LCR, reverse transcriptase initiated PCR, DNA or RNA hybridization, genomic sequencing, and other methods of subsequent analysis are known in the art.

In another embodiment of the invention, a sample of GM associated with proteins or hemoglobin which is stored on the dry solid medium of the invention may be removed using aqueous extraction. One such aqueous extraction procedure uses aqueous SDS and mercaptoethanol. Specifically, the sample of GM stored on the dry solid medium of the invention, with or without components for subsequent analysis, is washed with an alkaline solution of aqueous 6% SDS at pH 8.5 to 9.0 which contains a thiol, for example, 20 mM 2-mercaptoethanol or dithiothreitol. The GM is then washed with iso-propanol to remove substantilly all remaining anionic detergent (e.g., using the aqueous alcohol wash solution described below for the single phase phenol wash).

As will be apparent to those skilled in the art, in situ subsequent analysis of GM stored on the dry solid medium of the invention with or without components for subsequent analysis is of particular benefit in automated systems. As used herein, an "automated system" includes "automatic fluid delivery systems." According to the invention, "automatic fluid delivery systems" include hand-held and robotic fluid delivery systems. Typically, automatic fluid delivery systems are devices which dispense and remove fluid reagents to and from individual wells of multi-well reaction plates. Hand-held automatic fluid delivery systems comprise a single plunger handle with multiple fluid aspirating and dispensing ends to simultaneously aspirate and dispense fluid of a fluid reaction system from single or multiple fluid reaction vessels simultaneously. Robotic automatic fluid delivery systems are computer operated rather than hand-held and include such products as, for example, BIOMEK 2000 (Beckman Instruments, Fullerton, Calif.), Zymark Benchmate (Zymark, Hopkinton, Mass.) and ROSYS PLATO, Rapperswil, Switzerland. Automated fluid delivery systems are also discussed in U.S. Ser. No. 08/320,041 which is incorporated herein by reference.

A. SINGLE PHASE PHENOL WASH

Another aspect of the present invention provides a nonaqueous extraction method for removing hemoglobin and/or proteins associated with a stored sample of GM. According to the invention, hemoglobin and proteins may be removed from a stored sample of GM using a single phase phenol wash. Preferably, the single phase phenol wash also removes components of the composition of the invention (e.g., anionic detergent). The single phase phenol wash is performed by contacting a single phase phenol solution with the dry solid medium having applied thereto a sample of GM. The single phase phenol wash is removed from the dry solid medium containing a sample of GM and the dry solid medium is then contacted with an aqueous alcohol wash. The aqueous alcohol wash is then removed. If the sample of GM is to be analyzed by PCR, LCR or other method which relies on ions, the sample of GM may then be contacted with an ionic aqueous alcohol wash prior to PCR analysis. As previously noted, a nonaqueous wash system such as the single phase phenol wash or an aqueous wash system may also be used to wash a sample of GM stored on a solid matrix, with or without included components for subsequent analysis, which does not have the composition of the invention sorbed thereto.

The single phase phenol wash provides for removing proteins and/or hemoglobin or components of the composition of the dry solid medium which may effect the subsequent treatment to be performed on the GM stored on the dry solid medium without effecting the stored GM. Unlike prior art methods, the present wash system does not require two phase separations (aqueous and organic phase) during processing and tends not to dissolve GM present in blood. The single phase phenol wash is also amenable to automated systems.

The single phase phenol wash is also disclosed in U.S. patent application Ser. No. 08/159,104. The wash includes two solutions, referred to below as "single phase phenol solution" (solution A) and "aqueous alcohol wash solution" (solution B). A third solution, "ionic aqueous alcohol wash solution" (solution C), may be used, after the single phase phenol wash if the sample of GM is to be analyzed using a method which requires additional ions, for example, PCR and LCR.

Solution A: The single phase phenol solution (also referred to as water unsaturated phenol wash) includes phenol and hydroxyquinoline saturated with Tris-acetate and mercaptoethanol. Preferably, 50 grams (gm) of phenol is combined with 120 milligram (mg) of 8-hydroxyquinolone saturated with 10 milliliter (ml) of 1.0 molar (M) Tris-acetate at pH 6.0 to 9.0, preferably pH 8.0, and 1.0 ml 2-mercaptoethanol. After saturation by shaking at a temperature of about 0° C. to 200° C., preferably 0° C. to 40° C., the aqueous phase is removed and discarded.

Solution B: The aqueous alcohol wash solution utilizes any $C_2$–$C_5$ alcohol, such as isopropanol or n-propanol, or any other similar water miscible solvent combined with an acetate salt or similar organic soluble salt which provides a pH of about 7.0 to 9.0, preferably about pH 7.8. In a preferred embodiment 75% by volume isopropanol is combined with 25% by volume of 0.1M potassium acetate at a pH of about 7.8.

Solution C: The ionic aqueous wash solution is a wash solution which provides appropriate ions, for example, magnesium, manganese, sodium, protamine, tris and similar ions which may be useful in a subsequent analysis procedure. For PCR analysis, magnesium is preferred. Accordingly, the ionic alcohol wash solution utilizes any $C_2$–$C_5$ alcohol, such as isopropanol and n-propanol, or any other similar water miscible solvent combined with an acetate salt or similar organic soluble salt which provides a pH of about 6.0 to 8.5, preferably about pH 7.8. In a preferred embodiment for magnesium ions, 75% by volume isopropanol is combined with 25% by volume of 0.01M magnesium acetate at a pH of about 7.5.

According to the invention, a sample of GM associated with hemoglobin and/or protein which is stored on the dry solid medium is contacted with solution A for about 15 minutes to about 3 hours, preferably about 1.5 to about 2 hours, at a temperature which is greater than 37° C., preferably about 45–650° C., more preferably about 50° C. The temperature at which the sample of GM is contacted with solution A is not critical if the dry solid medium of the invention does not also include a component for subsequent analysis, such as a primer, which is discussed below. The solution A is then removed. Preferably, the sample of GM is then quickly washed 1–4 times, for a few seconds each time with fresh solution A.

After removal of solution A, the sample of GM is washed, for a few seconds, 1–4 times with solution B. Preferably, the solution B washes are at about 10° C. to 25° C. If solution C is to be used, after solution B is removed, solution C is applied to the sample of GM for about 1–60 minutes, preferably about 30 minutes, at a temperature of about 10° C. to 25° C. The solution C is removed and the sample of GM on the dry solid medium is dried.

Generally, the single phase phenol wash of the invention provides a substantially protein and/or hemoglobin free GM that provides a very convenient starting point for a variety of analytical procedures based on nucleic acids. The use of the single phase phenol wash and ionic aqueous alcohol wash is further described in the Examples.

According to the invention, the single phase phenol wash may be used to provide a substantially protein/hemoglobin free sample of GM stored on any solid system. Moreover, as described below, the single phase phenol wash is of particular benefit when a solid storage system incorporates components for subsequent analysis such as primers. Hence, the single phase phenol wash is useful to remove proteins and/or hemoglobin from a sample of GM stored on a storage medium regardless of whether or not the storage medium incorporates the GM protecting composition of the invention and regardless of whether or not the storage medium includes components necessary for subsequent analysis.

B. DRY SOLID MEDIUM INCLUDING COMPONENTS FOR SUBSEQUENT ANALYSIS OF GENETIC MATERIAL

In another embodiment of the invention, the dry solid medium includes components for subsequent analysis of a stored sample of GM. As previously stated, "subsequent analysis" means any analysis which may be performed on a sample of GM stored on the dry solid medium. This includes chemical, biochemical or biological analysis. Examples of subsequent analysis which may be performed on samples of GM stored on the dry solid medium include PCR, LCR, reverse transcriptase initiated PCR, DNA or RNA hybridization techniques including RFLP and other techniques using genetic or DNA or RNA probes, genomic sequencing, enzymic assays, affinity labeling, method of detection using labels or antibodies and other methods known in the art.

As used herein, "components for subsequent analysis of a stored sample of GM" includes a molecule, compound, reagant or other component which may be functional in analyzing, or preserving for analysis, a sample of GM, or analysis of some other component stored with the GM on the dry solid medium. In some instances, subsequent analysis will involve an analytical method which is used to establish the absence or presence of a particular genetic sequence. The genetic sequence to be analyzed is termed a "target sequence." The target sequence or other region of a sample of genetic material may serve as a "template" for PCR amplification.

One or more component may be included on the dry solid medium. The component(s) included on the dry solid medium is dependent on the particular analysis to be performed on the sample of GM. The advantage of including a component functional in the subsequent analysis of a sample of GM is readily apparent in situations where large numbers of samples GM are simultaneously analyzed using automated systems. An example of a component which may be included on a dry solid medium is a "nucleotide sequence."

As used herein, nucleotide sequence includes a primer, (e.g., a PCR primer, a primer for reverse transcriptase initiated PCR), sets of oligonucleotide substrates for LCR, DNA or RNA probe, oligonucleotides used in genetic sequencing, or target sequence stabilizer.

As used herein, a "primer" means one pair of oligonucleotides, each of which is capable of annealing to a complementary nucleic acid sequence in a sample of GM, and which are oriented so that each primer will prime the synthesis of a strand of DNA (or conceivably, a strand of RNA) containing a sequence complimentary to the other oligonucleotide. For some applications, it is desirable that the sequence of the oligonucleotide and its complimentary sequence is predetermined. In other applications, the sequence may be unknown. A plurality of degenerate primers or primers with sequences predicted to bind to the compliementary sequence may be used. The primer-pair may be used to amplify a pair of complimentary sequences and the sequence between the two complimentary sequences of known or unknown size. In addition, the primer may be used to amplify a template that is initially double-stranded DNA or RNA, as well as single-stranded DNA or RNA. For a single-stranded template, it is understood that the sequence complementary to one of the oligonucleotides will be synthesized by elongation of the first primer as it is annealed to its complementary sequence.

Primers for PCR or for reverse transcriptase initiated PCR may be present as a primer-pair, as is usual, or there may be only one primer as may be the case with genomic-sequencing or some protocols for reverse transcriptase initiated PCR.

In another embodiment of the invention, a component for subsequent analysis may be a nucleotide sequence referred to as a "target sequence stabilizer." A target sequence stabilizer may be beneficial for enhancing storage of an unstable single strand RNA or DNA stored as a sample of GM on the dry solid medium. According to this embodiment, a "target sequence stabilizer" is a nucleotide sequence which may be complimentary to an entire region of RNA or DNA which is to be analyzed. As is known in the art, many single strand RNAs are unstable and vulnerable to degradation by low levels of omnipresent RNases. However, the inventors believe that by including a target sequence stabilizer on the dry solid medium, the target sequence stabilizer binds to the single strand RNA (or DNA) sample and the "hybrid" formed is less vulnerable to degradation. For example, it is known in the art that double-stranded RNA/DNA hybrids are highly resistant to the common RNAases. The RNA or DNA annealed to the target sequence stabilizer may then be further analyzed using methods known in the art, for example, LCR or combinations of LCR and reverse transcriptase initiated PCR.

Therefore, according to the invention, components for subsequent analysis of a stored sample of GM includes components which function in subsequent analysis of a sample of GM as well as provide further protection of a stored sample of GM such that the GM is available, in nondegraded form, for subsequent analysis. The inclusion of a nucleotide sequence on the dry solid medium provide significant advantages for simplifying subsequent analysis of GM by, for example, automated PCR systems. In addition, selection of appropriate nucleotide sequences may provide additional protection from degradation of GM material such as unstable RNA.

Other components for subsequent analysis of stored GM which may be included in the dry solid medium of the invention are, for example, genetic probes or olignucleotide or polynucleotide sequences with labels of diverse types. Labels may include a fluorescent chemical group, radioactive isotope, chemical binding agent (e.g., biotin), antigens or enzymes.

PCR amplification of a stored sample of GM, for example, blood DNA, is greatly simplified using the dry solid medium of the invention including a nucleotide sequence such as a primer. Furthermore, utilizing the single phase phenol wash of the invention to remove proteins and/or hemoglobin associated with a sample of GM on a dry solid medium which includes a nucleotide sequence, provides for insubstantial loss of the included nucleotide sequence. By "insubstantial" it is meant that the wash, when completed, has not caused sufficient loss of primer to prevent PCR, LCR, reverse transcriptase initiated PCR, probing, etc. Hence, because both the nucleotide sequence and sample of GM remain entrained to the dry solid medium during the washing procedure, in situ processing is possible. This provides a significant advantage for GM analysis using automated systems.

In the case of PCR amplification, for example, by including a primer necessary for amplifying a specific DNA or RNA gene sequence, multiple samples containing different primers may be analyzed using a single PCR reaction mixture. Typically, only one mixture of PCR enzyme and nucleotides to all vials is necessary. Moreover, even if different primers included with different GM samples require variation in reaction conditions such as magnesium ions and/or pH, these variations can be accommodated with only two additional pump or pipette systems to deliver inexpensive salts and buffers that will cover most contingencies.

The components for subsequent analysis are preferably included on the dry solid medium before subsequent treatment of the GM. Various permutations for inclusion of the components are possible. For example, the components may be added and mixed with the composition of the dry solid medium prior to application of the composition to the solid matrix. Also, the primers may be added to the solid matrix simultaneously with the composition. Alternatively, the composition of the invention may be applied to the solid matrix and the primers applied subsequently. In another alternative, a sample of GM may be applied to the dry solid medium and a component applied to the dry solid medium after collection of the sample of GM but before removing any hemoglobin or protein associated with the GM sample. It is also foreseeable that a component may be added to the dry solid medium after removing protein and/or hemoglobin but before subsequent analysis.

Thus, the invention provides for novel and previously impractical strategies to be made feasible by a dry solid medium including a component for subsequent analysis in combination with methods that allow for co-processing the component with the stored GM.

C. INCLUSION OF MULTIPLE NUCLEOTIDE SEQUENCES ON A SINGLE DRY SOLID MEDIUM

The dry solid medium of the invention may also be identified or referred to as a card. A card may be prepared in such a manner as to provide different components for subsequent analysis at different locations on a single card. When the component for subsequent analysis is a nucleotide sequence, multiple different nucleotide sequences for priming amplification or stabilizing different target sequences may be stored on one card. As used herein, "multiple" means greater than one. For example, a single sample of GM to be analyzed may be stored on a single card which is about 1 mm to 5 mm square. Therefore, a card which is about 5 cm×10 cm could be divided, for example, into 200 individual samples. Each individual 5 mm square could hold a different nucleotide sequence. Accordingly, a single 5 cm×10 cm card could provide for subsequent analysis using 200 different nucleotide sequences.

In a preferred embodiment, a nucleotide sequence included on a card for subsequent analysis is a primer. According to this embodiment, a dry solid medium card may incorporate all or many of the primers for a particular application on a single card. For example, one application may be to screen for various target sequences, in a single GM sample, which are all involved in a particular genetic disease. Hence, an unlimited range of pre-made and pre-labelled sample-receiving cards may be held at a collection center ready for samples of GM such as blood. These cards, including primers, may be labelled, packaged and sold for particular categories of usage and put together in defined-purpose-folios (e.g., a card for standard penitentiary purposes or a card screening for various diseases of genetic origin). Moreover, the inclusion of a primer on the card allows the dry solid medium to be employed in a variety of different fields and still be conveniently processed together at one centralized, unspecialized center for automated analysis. This will allow the automated system to use one basal mixture of enzyme, and possibly buffer, to simultaneously amplify all target sequences for which primers are present on one type of card. As previously noted, the potential variations in ions and pH can be handled through a variety of ways, for example, separate delivery pumps or the use of the newer pellet-delivery of magnesium or other substances in wax.

EXAMPLES

Example 1

In situ PCR Amplification of Blood DNA Stored on Dry Solid Medium

A sample of blood DNA stored on the dry solid medium of the invention was amplified in situ by the polymerase chain reaction (PCR) technique. The dry solid medium used in this Example was cellulose based paper having sorbed thereto a composition comprising, per sq.cm of paper, 2 micromols uric acid, 8 micromols tris (free base), 0.5 micromols EDTA and 1 mg SDS. The stored blood was washed and suitable ions added prior to PCR amplification.

1.1 Single Phase Phenol Wash

A. Materials

Solution A:

Single-phase phenol wash solution. A suitable mixture is phenol, 50 gm containing 120 mg of 8-hydroxyquinoline that has been saturated with 10 ml of 1.0 M tris-acetate pH 8.0 and 1.0 ml 2-mercaptoethanol. After saturation by shaking at room temperature, the aqueous phase is thoroughly removed and discarded.

Solution B:

Aqueous alcohol wash solution. 75% v/v Isopropanol, 25% v/v 0.1M potassium acetate at pH 7.8.

Solution C:

Ionic aqueous wash solution. 75% v/v Isopropanol, 25% v/v 0.1M magnesium acetate.

B. Method

All steps are preferably carried out in a single tube made of a suitable phenol resistant material, e.g. polyethylene.

1. Removal of protein: a 5 mm×5 mm square of blood impregnated dry solid medium was treated with 1 ml of solution A, for approximately 1.5 hours at 45° C. (since no primers were present, this temperature and time is not critical). The solution A was then aspirated to waste and the paper square quickly washed three times with 0.25 ml of solution A. Each wash was for only a few seconds and was immediately aspirated to waste.

2. Removal of phenol and addition of suitable ions: the dry solid medium from step (a) above, was rapidly washed three times with 1 ml of solution B. Washes were at room temperature and were simple additions followed by aspiration to waste. The paper was then washed for 20 minutes at room temperature with solution C. (This is to saturate the GM on the paper with magnesium ions and remove the last of the phenol.) The solution C is aspirated to waste and the dry solid medium was solvent-dried with one wash of pure isopropanol and then vacuum dried.

The washed dry solid medium was relatively quite white without any obvious remnants of the red-brown color of blood. It was then used in a PCR reaction mix.

1.2 Amplification of DNA on Dry Solid Medium

The washed sample on dry solid medium described above has been shown to be a suitable substrate for DNA polymerase chain reaction (PCR) amplification of DNA.

A. Materials

1. Specimens

Extracted DNA: 10 ml of blood was removed from a male volunteer using standard protocols.

Dry solid medium: Blood samples from the same volunteer were applied directly to the dry solid medium with subsequent single phase phenol washing as described above. The dry solid medium was cut into about 1 mm×1 mm pieces for use in PCR reactions.

2. Targets for Amplification

Target No. 1: Region of exon 2 of the n-Ras protooncogene on chromosome 1. The primers used are:

R1: 5' TGA CTG AGT ACA AAC TGG TGG TG 3' (SEQ ID NO:1)

R2: 5' CTC TAT GGT GGG ATC ATA TTC A 3' (SEQ ID NO:2).

The amplified DNA fragment obtained with these primers is 110 bp in size.

Target No. 2: A male specific Y chromosome repeat sequence. The primers are:

007: 5' TGG GCT GGA ATG GAA AGG AAT GCA AAC 3' (SEQ ID NO:3) and

008: 5' TCC ATT CGA TTC CAT TTT TTT CGA GAA 3' (SEQ ID NO:4). The amplified DNA fragment obtained with these primers is 124 bp in size.

Target No. 3: A male specific Y chromosome repeat sequence. The primers used are:

004: 5' GAA TGT ATT AGA ATG TAA TGA ACT TTA 3' (SEQ ID NO:5) and

006: 5' TTC CAT TCC ATT CCA TTC CTT TCC TTT 3' (SEQ ID NO:6).

The amplified DNA fragment obtained with these primers is 250 bp in size.

B. Method

1. PCR Protocol

Extracted DNA (1 μg) or about 1 mm×1 mm fragments of washed dry solid medium containing a sample of blood DNA were placed into 0.5 ml Eppendorf tubes and made to 25 μl in PCR reaction mixture consisting of:

67 mM Tris HCl (pH 8.8 @ 25° C.)

16.6 mM $(NH_4)_2 SO_4$ 2.0 mM $MgCl_2$ 0.01% (w/v) gelatin 0.1 mM deoxynucleotide (dATP, dTTP, dCTP, dGTP)

0.25 μg of each primer (for respective target)

0.25 U of Taq DNA polymerase.

2. The amplification conditions The mixture was overlaid with 25 μl of light mineral oil and DNA amplification was performed by 30 cycles of amplification on a Perkin Elmer-Cetus "thermal cycler". The first cycle consisted of:

| | |
|---|---|
| DNA denaturation | 6 min. @ 94° C. |
| Primer-DNA annealing | 1 min. @ 55° C. |
| Taq DNA polymerase extension | 1 min. @ 75° C. | followed by 29 cycles as above except DNA denaturation was for 1 min @94° C. and the extension time on the last cycle was 10 min @ 72° C. before cooling the reaction mixture to 4° C.
1.3 Results After amplification, 10 μl aliquots of PCR mixture were analysed by electrophoresis on 15% (w/v) polyacrylamide gels. Amplified target DNA was visualized by UV illumination of the ethidium bromide stained gel.

Figure 1:
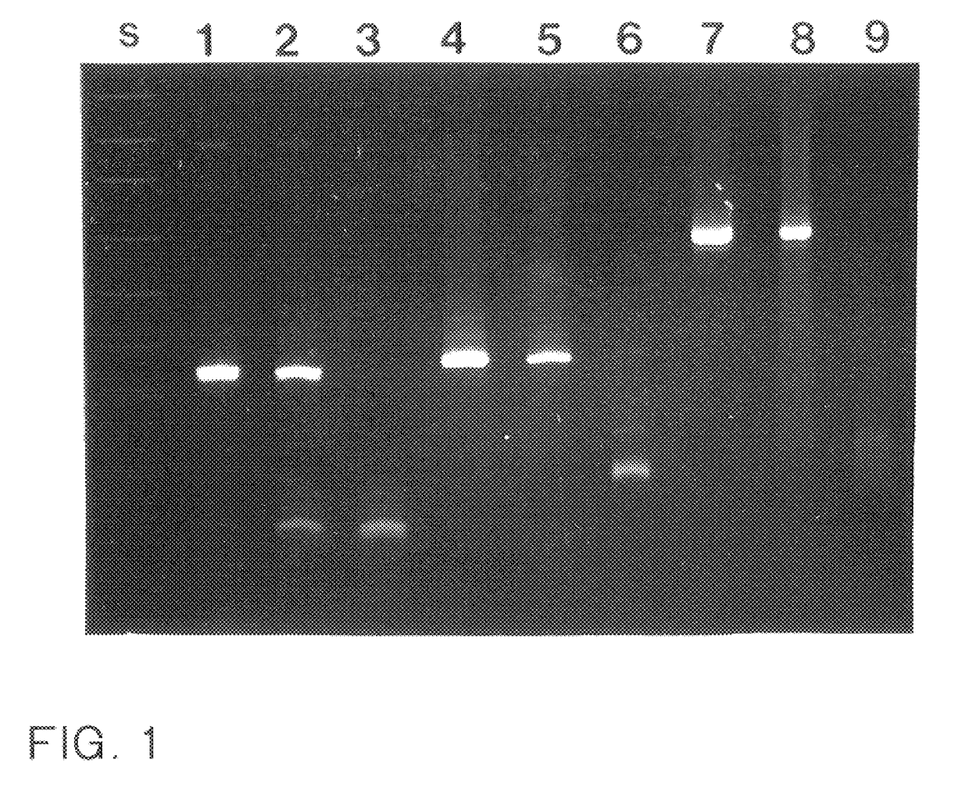
FIG. 1, Photograph of ethidium bromide stained gel of PCR amplified DNA from blood samples stored on a dry solid medium of the invention.

An analysis of the products from PCR amplification of extracted blood DNA and blood DNA stored on dry solid medium are shown in FIG. 1, as follows:

Lanes 1–3: target No.1, lane 1: 1 μg DNA, lane 2: 1 mm² filter, lane 3: control (no DNA);

Lanes 4–5: target No.2, lane 4: 1 μg DNA, lane 5: 1 mm² filter; Lane 6: control (no DNA);

Lanes 7–9: target No.3, lane 7: 1 μg DNA, lane 8: 1 mm² filter, lane 9: control (no DNA);

lane S: DNA size markers (pUC19/HpaII digest).

The results shown in FIG. 1 clearly demonstrate that the DNA has not been changed in any way as a result of its storage on the dry solid medium of the invention, and that it can be used in situ as described herein.

Example 2
PCR Reactions on DNA Stored on Dry Solid Medium Including Primers

PCR analysis was performed on dry solid medium including primers added to the dry solid medium prior to the collection of a sample of blood DNA.

2.1 Genetic Material
A. Materials
 1. DNA Templates

For preparing samples of genetic material containing DNA, 3 μl of human blood was applied to a 3 mm square sample of dry solid medium, and the blood was allowed to dry. Unless otherwise indicated, this 3 mm square was then used in each PCR reaction. 3 μl of blood corresponds to approximately 250 nanograms of white-cell DNA. In addition, a control sample of purified human DNA in free solution was amplified using PCR.

2. Primers

Two synthetic oligonucleotide primers derived from the human Class II HLA gene, DQ-alpha, were used in the experiments. Their sequences are:

5' GTGCTGCAGGTGTAAACTTGTACCAG 3' (SEQ ID NO:7)

5° C.ACGGATCCGGTAGCAGCGGTAGAGTTC 3' (SEQ ID NO:8)

The size of the PCR product expected using the two primers is 262 bp. Each primer was stored as a stock solution at a concentration of 50 ng/ul. When added to the dry solid medium prior to processing, 150 ng of both primers was added to the 3 mm square of dry solid medium. The primers were always used together at equal concentrations.

2.2 Single Phase Phenol Wash

Solution A:

Single-phase phenol solution. 50 g of phenol, containing 120 mg of 8-hydroxyquinoline, was saturated with 10 ml of 1.0 M Tris-acetate pH 8.0 and 1.0 ml of 2-β-mercaptoethanol. After saturation at between 0° C. and 4° C., the aqueous phase was thoroughly removed and discarded.

Solution B:

Aqueous alcohol wash solution. 75% v/v isopropanol, 25% v/v 0.1M potassium acetate, pH 7.8.

Solution C:

Ionic aqueous wash solution. 75% v/v isopropanol, 25% v/v 0.01M magnesium acetate.

B. Method
 1. Washing the Dry Solid Medium

Samples of genetic material stored on the dry solid medium including a primer were processed by first washing the medium with 200 μl of Solution A for two hours at either 37° C. or 50° C., followed by two quick rinses of the aqueous phase with Solution A. The medium was next rinsed three times for five minutes each with 200 μl of Solution B at room temperature. The medium was then washed with 200 μl of Solution C for 20 minutes at room temperature and then dried under vacuum. (The wash times were all in excess. In practice, shorter times may be used. The effectiveness of the washes may be monitored by observing loss of color: (1) the hemoglobin; and (2) the hydroxyquinoline.)

2.3 PCR Protocol
A. Materials
 1. The Example PCR Mix 50 μl.

The following mixture was placed on washed dry solid medium containing a sample of blood before heatcycling:

67 mM tris-HCl, (pH 8.8 @25° C.)

16.6 mM $(NH_4)_2$ $SO_4$ 0.2 mg/ml gelatin 0.2 mg/ml gelatin 0.45% Triton X-100

2.0 mM MgCl2

0.2 mM each of dATP, dTTP, dCTP, dGTP 2.5 units Taq polymerase.

Template blood DNA was on dry solid medium or purified human DNA as free solution. (50 ng template added when in free solution.)

As shown in table 1, primers were included with the dry solid medium and/or in free solution. (100 ng each primer was if added as free solution.)

B. Methods
 1. The Amplification Conditions 4 min. @ 94° C. (start conditions)

1 min @ 94° C.

40 sec. @ 50° C. (32 cycles)

1 min. @ 72° C.

4° C. (soak-end conditions)

The expected product is a 242 bp segment of the human class-II HLA gene, DQ-alpha.

2. Electrophoresis Conditions

Electrophoresis was in 1 agarose, 0.045 M tris, 0.045 M Boric acid, 1 mM EDTA, pH 8.0, 1.5 hours at 8.5 volts/cm.

C. Results 3 mm×3 mm primer-loaded dry solid medium were taken. 3 μl of freshly collected human blood from one donor was placed on all dry solid medium samples and allowed to dry. It was then stored at room temperature for 7 days.

The squares of dry solid medium were then washed using the single phase phenol wash and all media-squares then dropped into PCR mixes either with or without added primers. There were thus trials in which the primers were added to the medium before loading blood to the medium, after loading blood to the medium, and to the final PCR mix (see Table 1).

After the cycling 8 μl samples of each reaction mix were electrophoresed with Promega PCR marker mix (Promega Corp., Madison, Wis.). (Bands at 1000 bp, 750 bp, 500 bp, 300, 150, 50.) The gel was stained with ethidium bromide and the product bands photographed (see FIG. 2).

Figure 2:
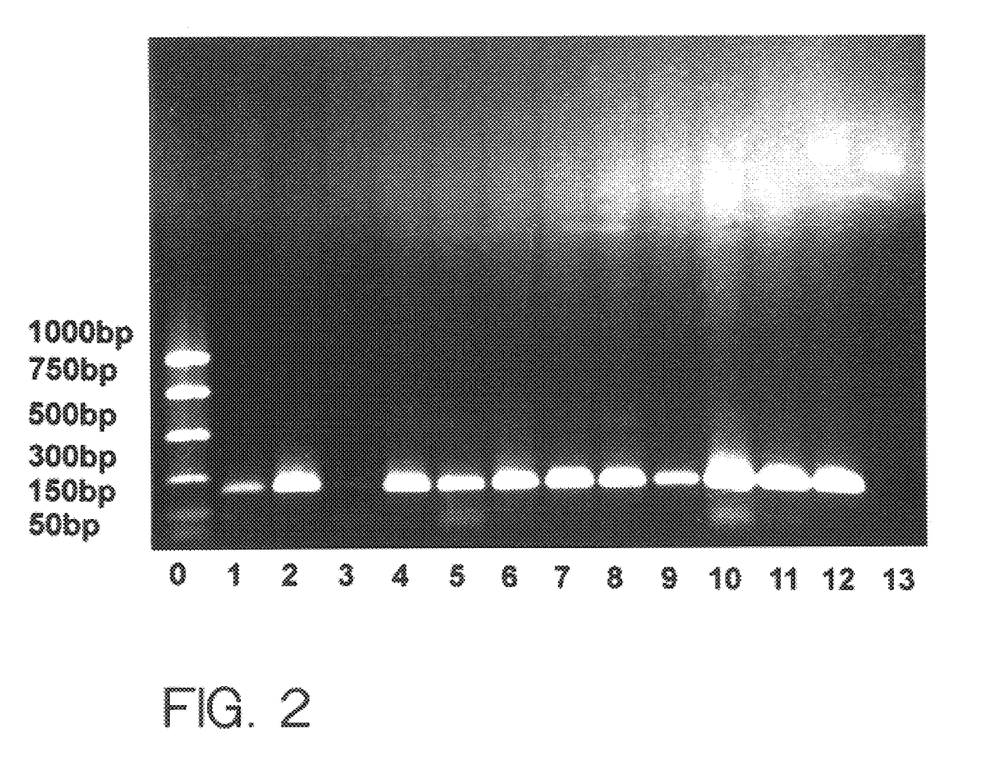
FIG. 2, Photograph of ethidium bromide stained gel of PCR amplified DNA from blood samples stored on a dry solid medium of the invention which included oligonucleotide primers for PCR analysis.

Four samples were processed with the single phase phenol wash taking place at 37° C., and four samples were processed with the single phase phenol wash taking place at 50° C. Subsequent processing steps and PCR reaction conditions for the two sets of samples were identical. FIG. 2 shows that extractions performed at 37° C. generated bands of the predicted size, and whose intensities varied (lanes 1–4), while extractions performed at 50° C. yielded intense bands of the predicted size (lanes 5–8). To show that the PCR products on DNA recovered from the dry solid medium were specific and corresponded to the expected PCR product, PCR reactions were performed on human DNA purified using standard methods (FIG. 2, lane 12), or using no DNA (FIG. 2, lane 13). No product was observed if no exogenous DNA was added to the reaction (FIG. 2, lane 13), and the product obtained with purified DNA comigrated with the PCR product obtained from processed samples of medium (FIG. 2, compare lanes 11 and 12).

Two additional sets of samples were then extracted at 37° C. To one reaction primers were added to the dry solid medium after the blood. To a second reaction primers were likewise added to the dry solid medium after the blood, and additional primers were added just prior to the beginning of the PCR reaction. The results of this experiment are shown in FIG. 2, lanes 9 and 10, respectively. Lane 9 reveals that the DNA on the dry solid medium generated a PCR product of the expected size when primers are added to the dry solid medium after the collection of the blood sample. A more intense PCR product of the expected size was obtained when primers were added just prior to performing the PCR reaction (compare lanes 9 and 10). The results of these experiments are summarized in Table 1.

TABLE 1

Experimental Conditions of PCR Reactions on DNA Stored on Dry Solid Medium

| Source of Template DNA | Time of Addition of Primers | Phenol Wash Temperature | Lanes in FIG. 2 | Mean Results of PCR |
|---|---|---|---|---|
| Human blood on washed dry solid medium | A | 37° C. | 1–4 | ++ |
| Human blood on washed dry solid medium | A | 50° C. | 5–8 | ++++ |
| Human blood on washed dry solid medium | A | 50° C. | 11 | ++++ |
| Purified human DNA in solution | D | N.A. | 12 | ++++ |
| No DNA | D | N.A. | 13 | — |
| Human blood on washed dry solid medium | B | 37° C. | 9 | +++ |
| Human blood on washed dry solid medium | C | 37° C. | 10 | ++++ |

KEY:
A = Primers included on dry solid medium before collection of blood sample.
B = Primers included on dry solid medium after collection of blood on the medium.
C = Primers included on dry solid medium after collection of blood on the dry solid medium, and additional primers added just prior to PCR reaction.
D = Primers added just prior to PCR reaction.
N.A. = Not applicable.
++++ = Intense bands.
+++ = Moderately intense bands.
++ = Moderate bands.
+ = Weak bands.

In summary, the use of the dry solid medium containing primers is clearly practical, it opens a window of technique that makes large-scale PCR analysis much more practical and amenable to less skilled labor, and opens potential new applications, with unstable templates.

Example 3

In situ Digestion of Stored Blood with Restriction Endonuclease Eco R1.

To determine if samples of blood DNA stored on a cellulose-based dry solid medium were digestible in situ with restriction endonucleases, and thus suitable for procedures such as RFLP analysis, samples of blood were collected on cellulose-based dry solid medium, washed with single phase phenol wash and digested with the restriction enzyme Eco R1. In this experiment, samples of blood were stored on the dry solid medium for as long as 18 months prior to processing.

3.1 Single Phase Phenol Wash

A. Materials and Methods

The single phase phenol wash and other wash solutions are described in Example 1 and 2. 1.5 ml of solution A was added to a dried 10 mm×10 mm piece of dry solid medium containing approximately 0.1 ml of dried human blood, and the solution was mixed using a standard laboratory mixer and incubated at 37° C. for 30 minutes. The solution A was then removed by aspiration and fresh solution A added. Treatments with solution A were repeated until all the heme color disappeared from the dry solid medium.

Next, the samples were washed five times with solution B for two minutes each, then twice with solution C, also for about two minutes each. Between each wash, the medium sample was subjected to centrifugal stripping. For this the medium was briefly spun in a small microfuge tube in which a hole had been pierced and which had been nested inside a larger microfuge tube. The medium was then dried under vacuum or, alternatively, by centrifugal stripping. Following the processing steps the samples which initially were black after application of the blood and subsequent drying, were white.

3.2 Digestion of Samples Stored on Dry Solid Medium Using Restriction Enzymes

A. Material

Restriction enzyme Eco R1 were used in buffers supplied by Boehringer Manheim.

B. Method

The washed dry solid medium was moistened with 50 μl of restriction enzyme buffer containing an excess of restriction enzyme. For digestions with the restriction enzyme Eco R1, 60 units of enzyme was added. To ensure complete wetting, the medium was wet in the buffer, centrifugally stripped, and remoistened with the buffer and enzyme mix. Digestions proceeded for 2.5 hours at 37° C.

The restricted DNA was stripped from the medium by first centrifugally stripping the medium and collecting the stripped fluid. DNA was then further removed by washing the solid medium with 25 μl of 7.5M ammonium acetate, followed by a wash with 25 μl of 2.5M ammonium acetate. At each wash step the medium was subjected to centrifugal stripping in order to maximize recovery of the fluids. The fluids from the wash steps were combined in a final volume of about 100 μl. The DNA was precipitated from the collected fluid by adding 250 μl of ethanol, and air-drying the final pellet. The pellet was resuspended in 20 μl of water, and 10 μl of the resuspended pellet was used in gel electrophoresis.

3.3 Gel Electrophoresis

A. Conditions for Gel Electrophoresis

Digestion products were electrophoresed in a 1.5% agarase gel prepared in Tris-Acetate (composition was 0.01M Tris, 0.005M sodium acetate, 0.5M EDTA adjusted to pH 7.8 with acetic acid) at 50 V, 80 mA for 2 hours, after which the gel was stained with ethidium bromide and photographed. (See FIG. 3).

3.4 Results

Figure 3:
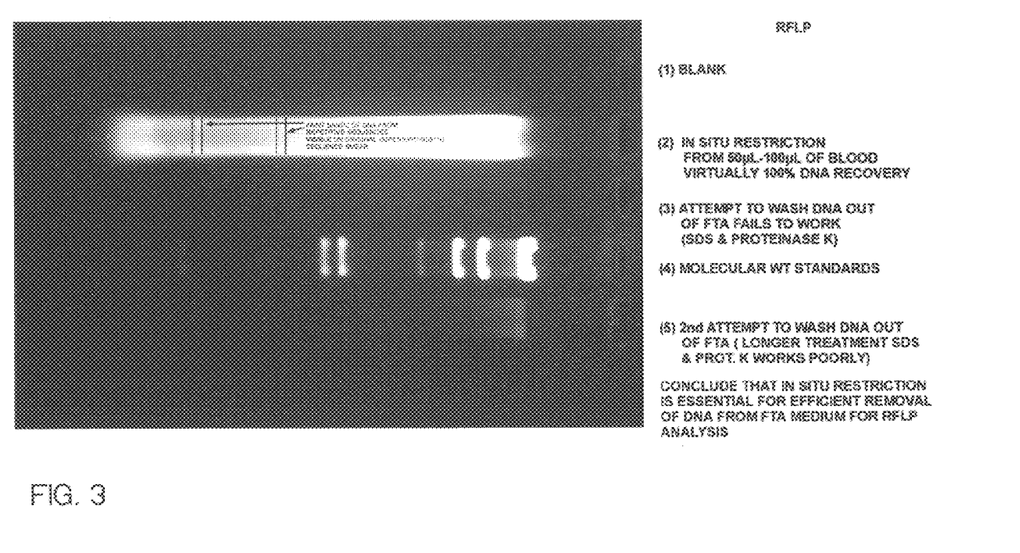
FIG. 3, Photograph of ethidium bromide stained gel of Eco R1 digestion of DNA from human blood stored on the dry solid medium of the invention.

To determine if blood samples stored on media of the invention for extended periods of time could be digested with restriction enzymes, samples of cellulose-based dry solid medium to which blood had been added 19 months previously, 11 months previously, or two weeks previously were processed and then digested with Eco R1. FIG. 3 contains a photograph of the ethidium staining pattern and reveals a smearing pattern characteristic of an Eco R1 digest of human DNA. Thus, DNA stored on the medium for at least 19 months is digestible with restriction endonucleases.

Example 4
Inactivation of Herpes Simplex Virus Type I and other microorganisms, by the Dry Solid Medium In these experiments dry solid medium prepared according to the invention was tested for its ability to inactivate herpes simplex virus, type I (HSV). HSV type I was chosen because it is a relatively resistant to inactivation and is transmissible through blood and other bodily fluids.

4.1 Isolation of HSV Virus

A. Materials and Method

A recent clinical isolate of HSV type I recovered from an eye lesion was grown to high titre ($>10^8$ plaque forming units/ml) in tissue culture flasks of HEp2 epithelial and MRC-5 fibroblast cells, harvested off the flasks, and sonicated to release intracellular virus. Viral particles were concentrated by high-speed centrifugation of a clarified supernatant of the sonicate and were resuspended in viral transport medium (VTM) containing 0.2M sucrose in a 0.02M phosphate buffer (pH 7.6), 10% fetal calf serum, and antibiotics.

4.2 Application of Viral Particles to the Dry Solid Medium and Subsequent Recovery For experiment I, the crude viral preparation was diluted 1:10 in either VTM or in fresh, heparinized blood. A 10 $\mu$l sample of the dilution was tested in duplicate on both untreated 10 mm×10 mm pieces of untreated cellulose based paper and also on 10 mm×10 mm square pieces of dry solid medium prepared according to the invention. After application of virus, the squares were supported in air by fine forceps, and after the appropriate time interval, the virus was eluted from the squares by vigorous agitation in 1 ml of MRC-5 maintenance medium (MM) (Eagles MEM based medium with Earle's salts) containing 2% fetal calf serum.

In experiment II, a stock virus was taken from storage at −70° C. and diluted 1:4 in citrated blood.

4.2 Assaying viral infectivity

A. Material and Method

The eluate was tested for infectivity using a fluorescent focus assay. Samples were diluted 1:100 in MM, and 0.2 ml of the dilution was then added to a well of MRC-5 fibroblasts in a 48-well cluster tray. After a 45 minute incubation at 37° C., the sample was replaced with 0.5ml MM and the tray was incubated overnight at 37° C. in the presence of 5% CO2. Cells were then fixed, stained with fluorescein-conjugated antibody to HSV, and the number of fluorescent foci was counted under a reverse-stage fluorescent microscope.

4.3 Results and Discussion

HSV type 1 viral particles were added either to untreated cellulose based paper or to cellulose based paper treated according to the invention to produce the dry solid medium, and then eluted after varying lengths of time. In one experiment, the virus was stored in VTM, and in the second the virus was resuspended in blood. The results of the experiment are shown in Table 2. In both experiments, viral infectivity was reduced to undetectable levels—in these conditions, greater than 99.5% inhibition—when virus was added to the dry solid medium, even when the viral particles were eluted immediately. Viruses in blood eluted from untreated cellulose based paper (CBP), in contrast, were only slightly, if at all, inhibited. A similar inhibitory effect on HSV infectivity was observed when the experiments were performed with viruses recovered from a frozen stock.

The invention has also shown the inhibitory effect of the dry solid medium on growth of

*Staphlococcus aureus, Staphlococcus epidermidis* and adventitious microorganisms in the environment.

TABLE 2

Infectivity of HSV Following Application on to Untreated cellulose based paper (CBP) Paper or on to Dry Solid Medium.

| Treatment | Viral Titer | Per Cent Inhibition | Viral Titer | Per Cent Inhibition |
|---|---|---|---|---|
| | A. HSV in VTM | | B. HSV in Blood | |
| Untreated (virus added directly to MM) | $1.9 \times 10^7$ | 0 | | — |
| Virus spotted on treated CBP and immediately eluted into MM | $<5.0 \times 10^4$ (no virus detected) | >99.5 | $<5 \times 10^4$ (no virus detected) | 99.5 |
| Virus spotted on untreated CBP and immediately eluted into MM | $1.2 \times 10^7$ | 37 | $9.8 \times 10^6$ | 48 |
| Virus spotted on treated CBP and eluted onto MM after 10 minutes | $<5 \times 10^4$ (no virus detected) | >97 | $<5 \times 10^4$ (no virus detected) | >97 |
| Virus spotted on untreated CBP and eluted into MM after 10 minutes | $1.8 \times 10^6$ | 90 | $9.7 \times 10^6$ | 47.5 |

Example 5
Method for treating the dry solid medium of the invention for use in standard analysis systems.

The dry solid medium of the invention, with or without components for subsequent analysis can also be used in standard assays of analytes for diagnostic purposes, e.g., in the Guthrie Test for phenylketonuria (PKU) and enzymic assays such as a test for galactosemia. Both of these tests are routinely carried out on newborn infants. Prior to analysis using such standard assay systems, it is preferable to neutralize the SDS and EDTA on the dry solid medium containing a sample of blood before the analysis of such analytes by adding a "converter solution".

5.1 Dry Solid Medium Converter Solution

The dry solid medium converter solution works by binding the SDS and EDTA.

A. Materials and Methods

The dry solid medium converter solution includes the following mixture:

1. 577 mg Protamine sulphate (salmine) Sigma No-4380, lot 71F-0037, is added to 7.69 ml water and shaken (to give 75 mg/ml).

This batch will be nominally 75 mg/ml before dialysis. This concentration is near to the solubility of the protamine. It dissolves slowly as a gluey turbid mass.

2. Dialysis: this is a clean-up precaution to assure that the material is essentially sterile and fully dissolved.

The gluey turbid mass is placed in a dialysis bag approx. 1.5 cm in diameter by 2 cm to 10 cm in length. Both ends of the bag are knotted tightly. The bag is then weighed and dropped into a 1 liter flask containing about 800 ml of 50 mM of magnesium acetate with chloroform and a stirring bar. The material is dialyzed in the flask, overnight, against the 800 ml of 50 mM magnesium acetate with an excess (approx. 5 ml) of chloroform present as a sterilizing agent. The protamine almost completely dissolves overnight giving a clear solution and few obvious small lumps of debris.

The weight of the bag increases:
Weight of bag before dialysis=8.1 g 20 hour dialysis, 4° with $CHCl_3$ saturated fluid.
Weight of bag after dialysis=8.67 g.
Thus, the concentration of protamine is now, nominally, 70 mg/ml. (Assuming no losses through bag.)

3. The bag was then punctured at the bottom, and the fluid collected and centrifuged at 4000 rpm (approx. 2000× g) for 10 mins. to remove debris.
4. 1 ml lots were stored at −80° C.
5. Prior to analysis, about 3 ul of the converter solution is applied to each 3 mm diameter disk of dry solid medium containing a sample of blood.

5.2 PKU Screening Procedure (Guthrie Test)

The Guthrie test is based on the stimulatory effect of phenylalanine on the growth of *Bacillus subtilis* in the presence of beta-2-thienylalanine growth inhibitor. Disks of blood samples are placed on agar containing bacterial spores and the inhibitor. Following incubation at 37° C. for 16 to 18 hours, the diameter of the growth around the disk is proportional to the concentration of phenylalanine. Higher than normal levels in infants is indicative of phenylketonuria.

An advantage of using the dry solid medium for the Guthrie test is that the disk of dry solid medium retains proteins and hemoglobin from the sample, leaving a cleaner area around the disk and making the interpretation of the result easier. In fact, samples of blood containing phenylalanine which were stored on the dry solid medium consistently gave at least as strong bacterial growth rings as equivalent samples on standard paper.

Also, because sufficient bacterial spores are used in a Guthrie test and the rate of growth is so fast, the inhibition or killing of bacteria by reagents of the dry solid medium which were proximal to the dry solid medium did not cause a problem for interpreting the results. Therefore, when using the dry solid medium it is not necessary to apply the converter solution to the disk prior to the test. However, it is an advantage to do this to remove an observable weak zone of growth inhibition.

5.3 Screening for Galactosemia

Galactosemia screening requires the use of active enzymes to assay for galactose and galactose phosphate. The main enzyme, beta-galactose dehydrogenase reduces NAD to NADH and this is observed spectrophotometrically.

This assay is severely inhibited by components of the composition of the dry solid medium, but the inhibition can be substantially eliminated by the application of converter solution to a sample of blood stored on the dry solid medium.

After addition of the converter solution, just prior to the enzymic assay, the assay has been observed to perform in the same way as it does with a sample of blood on untreated cellulose based paper. Of course, the dry solid medium has the advantage of providing the benefits of pathogen killing and preservation of the sample compared to standard materials used.

All patents and publications in the specification are indicative of the level of ordinary skill in the art to which this invention pertains. All patents and publications are herein incorporated by reference to the same extent as if each individual patent and publication was specifically and individually indicated by reference.

It will be apparent to one of ordinary skill in the art that many changes and modifications can be made in the invention without departing from the spirit or scope of the appended claims.

---

What is claimed is:

1. A dry solid medium for storage of at least one sample of genetic material, the dry solid medium comprising:
   (a) a solid matrix;
   (b) an effective amount of a composition which protects against degradation of DNA adsorbed or incorporated onto the solid matrix, said composition comprising:
      (i) a protein denaturing agent;
      (ii) a free radical trap; and
      (iii) a component functional in subsequent analysis of the sample of genetic material.

2. The dry solid medium according to claim 1 wherein the component functional in subsequent analysis of the sample of genetic material is a nucleotide sequence.

3. The dry solid medium according to claim 1 wherein the component functional in subsequent analysis of the sample of genetic material is a target sequence stabilizer.

4. The dry solid medium according to claim 1 wherein the component functional in subsequent analysis of the sample of genetic material is a PCR primer.

5. The dry solid medium according to claim 1 wherein the component functional in subsequent analysis of the sample of genetic material is added to the dry solid medium after the sample of genetic material is applied to the dry solid medium.

6. The dry solid medium according to claim 1 wherein the dry solid medium is a card comprising different components for subsequent analysis at multiple locations on the card.

7. The dry solid medium according to claim 6 wherein the component for subsequent analysis is a nucleotide sequence.

8. The dry solid medium according to claim 1 wherein the solid matrix is cellulose based.

9. The dry solid medium according to claim 8 wherein the solid matrix is nitrocellulose.

10. The dry solid medium according to claim 1 wherein the protein denaturing agent is a detergent.

11. The dry solid medium according to claim 1 wherein the free radical trap acts as a genetic material releasing agent to enhance release of the genetic material from the dry solid medium.

12. The dry solid medium according to claim 1 wherein the free radical trap is uric acid or a urate salt.

13. A method for storage of a sample of genetic material to be subsequently analyzed comprising:
   (a) applying a sample of genetic material to a dry solid medium, the dry solid medium comprising a solid matrix having sorbed thereto a composition comprising:
      (i) a protein denaturing agent;
      (ii) a free radical trap; and
      (iii) a component functional in subsequent analysis of the sample of genetic material; and
   (b) storing the sample of genetic material.

14. The method according to claim 13 wherein the component functional in subsequent analysis of the sample of genetic material is a nucleotide sequence.

15. The method according to claim 13 wherein the component functional in subsequent analysis of the sample of genetic material is a PCR primer.

16. The method according to claim 13 wherein the genetic material is RNA.

17. The method according to claim 13 wherein the component functional in subsequent analysis of the sample of genetic material is a target sequence stabilizer.

18. The method according to claim 13 wherein the genetic material is DNA.

19. The method according to claim 13 further comprising a step of analyzing the genetic material.

20. The dry solid medium according to claim 1 wherein the component functional in subsequent analysis of the sample of genetic material is included with the sample of genetic material that is applied to the dry solid medium.

* * * * *